United States Patent
Kane et al.

(10) Patent No.: US 6,846,322 B2
(45) Date of Patent: Jan. 25, 2005

(54) APPARATUS AND METHOD FOR MANIPULATING CORE BODY TEMPERATURE

(75) Inventors: John R. Kane, Scottsdale, AZ (US); Ryan M. Sims, Tempe, AZ (US); Scott Heneveld, Redding, CA (US)

(73) Assignee: Dynatherm Medical, Inc., Burlingame, CA (US)

( * ) Notice: Subject to any disclaimer, the term of this patent is extended or adjusted under 35 U.S.C. 154(b) by 0 days.

(21) Appl. No.: 09/990,069

(22) Filed: Nov. 21, 2001

(65) Prior Publication Data

US 2003/0097163 A1 May 22, 2003

(51) Int. Cl.[7] ................................................. A61F 7/00
(52) U.S. Cl. ..................... 607/111; 607/96; 607/104; 607/108; 607/109; 607/110; 607/112
(58) Field of Search .......................... 607/96, 104, 108, 607/109, 110, 111, 112

(56) References Cited

U.S. PATENT DOCUMENTS

| | | | | |
|---|---|---|---|---|
| 1,399,095 A | * | 12/1921 | Webb, Sr. ........................ 24/1 |
| 3,217,707 A | | 11/1965 | Werding |
| 5,241,958 A | * | 9/1993 | Noeldner ...................... 607/86 |
| 5,369,807 A | * | 12/1994 | Cho et al. ....................... 2/159 |
| 5,683,438 A | * | 11/1997 | Grahn ......................... 607/104 |
| 5,755,756 A | * | 5/1998 | Freedman et al. ........... 607/110 |
| 6,149,674 A | * | 11/2000 | Borders ........................ 607/96 |
| 6,277,143 B1 | * | 8/2001 | Klatz et al. .................. 607/104 |
| 2002/0007201 A1 | * | 1/2002 | Grahn et al. ................. 607/104 |
| 2002/0019653 A1 | * | 2/2002 | Grahn et al. ................... 607/96 |
| 2002/0022871 A1 | * | 2/2002 | Grahn et al. ................. 607/108 |

FOREIGN PATENT DOCUMENTS

WO   WO 98/40039 A1   9/1998
WO   WO 01/80790 A1   11/2001

OTHER PUBLICATIONS

Grahn, Dennis, et al., "Recovery from Mild Hypothermia Can Be Accelerated By Mechanically Distending Blood Vessels in the Hand," The American Physiological Society, (1998), pp. 1643–1648.

* cited by examiner

Primary Examiner—Rosiland Rollins
(74) Attorney, Agent, or Firm—Moser, Patterson & Sheridan, L.L.P.

(57) ABSTRACT

The present invention provides a system for manipulating a core body temperature of a mammal. The system of the invention includes a chamber for enclosing a body portion of a mammal and a seal in operative association with the chamber for sealing the chamber around the body portion and for inhibiting movement of the body portion relative to the chamber when the system is in operation. A thermal energy exchange system in operative association with the chamber includes an energy element assembly coupled to a flexible membrane assembly. The flexible membrane assembly facilitates an exchange of energy between the energy element assembly and the body portion. A vacuum system is operatively associated with the chamber while the thermal energy exchange system is in operation. The vacuum system generates a sub-atmospheric pressure within the chamber.

27 Claims, 12 Drawing Sheets

| Indicators | Status | Visible | Audible | Status | Visible | Audible |
|---|---|---|---|---|---|---|
| Vacuum | Proper | Yes-green light | No | Improper | Yes-yellow light | No |
| Temperature | Proper | Yes-green light | No | Over-temp | Yes-red light | Yes |
| Water Level | Proper | No | No | Under-filled | Yes-yellow light | Yes |
| Seal | Proper | Yes-green light | No | Improper | Yes-yellow light | No |

APPARATUS AND METHOD FOR MANIPULATING CORE BODY TEMPERATURE

FIELD OF THE INVENTION

The present invention relates generally to therapeutic devices and, more particularly, to therapeutic devices which may be used to manipulate the core body temperature of a mammal, such as a mammal whose core body temperature is outside its normal range.

BACKGROUND OF THE INVENTION

Homeothermic animals, such as humans, strive to maintain an internal or core body temperature that is within a comparatively narrow range regardless of the effects of external conditions or internal stresses. In humans, the thermal core generally includes the vital organs of the body, such as the brain and the several organs maintained within the abdomen and chest. Peripheral tissues, such as the skin, fat, and muscles, act as a buffer between the thermal core and the external environment of the animal by maintaining a temperature gradient that ranges from near-core temperature within internal tissues to near-ambient temperature at the surface of the animal.

Generally, the body compensates for minor fluctuations in body temperature through an autonomic thermoregulatory control mechanism that is triggered by temperature sensors located both in the body core as well as on the surface of the skin. For example, when the body experiences an upward shift in temperature, an involuntary response referred to as perspiration attempts to dissipate the excess heat by transferring moisture from body tissues to the body surface. Once at the surface, the moisture evaporates and carries with it some quantity of stored heat. Conversely, when experiencing a downward shift in temperature, the body attempts to generate heat by shivering, an involuntary contraction and expansion of muscle tissue throughout the body which creates heat through friction.

Hypothermia is a condition experienced by a homeothermic animal when the body is unable to generate sufficient heat to overcome external temperature conditions and the animal's core temperature falls below the normal range for the species. In extreme cases, a lowered core temperature renders it impossible for the body to maintain normal bodily functions. In humans, hypothermia may be defined as a core temperature of less than about 35° Celsius. Hypothermia may be caused when the body is overwhelmed by low environmental temperatures or is otherwise compromised, such as by being placed under general anesthesia, which induces a loss of the ability to conserve bodily heat. Hypothermia generally results in several physiological responses which attempt to prevent further heat loss. The most important of these responses is vasoconstriction, a constriction of the peripheral blood vessels which limits blood flow to the extremities and therefore reduces heat transfer away from the thermal core of the body. While vasoconstriction appropriately limits heat loss from the thermal core, it also makes it much more difficult to reverse a hypothermic state by applying heat to the surface of the body. That is, in restricting heat transfer from the core to the periphery of the body, vasoconstriction also impedes the transfer of heat from the body surface to the thermal core. This physiological impediment to heat transfer is referred to as a vasoconstrictive blockade to heat exchange.

U.S. Pat. No. 5,683,438, issued to Grahn and assigned to Stanford University, discloses an apparatus and method for overcoming the vasoconstrictive blockade to heat exchange by mechanically distending blood vessels in a body portion and providing for the transfer of heat to the body core of a hypothermic mammal. The disclosed device comprises a fluid-filled heating blanket that is lodged within a tubular, elongated sleeve which is placed over the body portion. The sleeve is maintained around the body portion of the patient by means of a flexible, tubular flange which seals around the body portion when sub-atmospheric pressure is applied and maintained within the sleeve. This system may be improved in several regards. First, more adequate means for securely fastening the device around body portions of varying diameter may be provided. Second, means in addition to the application of a vacuum within the sleeve may be provided to ensure optimal contact between the heating element and the body portion during treatment. Further, means for storing thermal energy within the sleeve may be provided so that the unit may be disconnected from the heat source without significant heat loss during patient transport.

In view of the foregoing, a need exists for an apparatus and method for manipulating the core temperature of a mammal which overcomes the shortcomings of the prior art. Accordingly, there is a need for an apparatus which adapts to the variability in patient sizes. There is also a need for a device which provides a means for securing the device around a body portion of a patient such that the body portion is inhibited from moving relative to the device during treatment. There is a further need for a device which optimizes contact between the heating element and the body of the patient, thereby optimizing heat transfer. Additionally, there is a need for a device which is capable of storing thermal energy such that the unit may be disconnected from the heat source without significant heat loss during patient transport.

SUMMARY OF THE INVENTION

The present invention provides a non-invasive technique for manipulating the core temperature of a mammal using a compact, self-contained apparatus that is readily applied to a body portion without interfering with access to the remainder of the body. The system of the invention comprises a chamber in which a body portion may be placed to mediate the exchange of thermal energy between the system and the thermal core of the mammal. The exchange of thermal energy is facilitated by a sub-atmospheric pressure created within the chamber such that the physiological state of the vascular structures of the body portion is mechanically manipulated to promote an exchange of thermal energy between the system and the thermal core of the mammal.

In an exemplary embodiment, a system for manipulating the core body temperature of a mammal comprises a chamber for enclosing a body portion of the mammal; a seal in operative association with the chamber for sealing the chamber around the body portion and for inhibiting movement of the body portion relative to the chamber; a thermal energy exchange system in operative association with the chamber, the thermal energy exchange system comprising an energy element assembly coupled to a flexible membrane assembly which facilitates an exchange of energy between the energy element assembly and the body portion; and a vacuum system which operates in coordination with the thermal energy exchange system, wherein the vacuum system generates a selected sub-atmospheric pressure within the chamber, thereby causing a dilation of vascular structures within the body portion and facilitating the exchange of energy via the treated body portion between the energy element assembly and the thermal core of the mammal.

BRIEF DESCRIPTION OF THE DRAWINGS

The present invention is illustrated by way of example, and not of limitation, in the accompanying figures, in which like references indicate similar elements, and in which.

Skilled artisans will appreciate that elements in the figures are illustrated for simplicity and clarity and have not necessarily been drawn to scale. For example, the dimensions of some of the elements in the figures may be exaggerated relative to other elements to enhance understanding of the various embodiments of the present invention.

DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that logical, mechanical, and electrical changes may be made without departing from the spirit and scope of the present invention. Thus, the following detailed description is presented for purposes of illustration only and not of limitation, and the scope of the present invention is defined solely by the appended claims.

Preliminarily, as used herein, the phrase "thermal energy exchange" shall be understood to mean the transfer of heat from the system of the invention to the thermal core of a mammal. More specifically, a "thermal energy exchange" includes the transfer of heat from the system of the invention to a treated body portion and then to the thermal core of the mammal. In this context, the mammal may be hypothermic, that is, the mammal may have a core temperature that is below that which is generally considered to be the normal range for its species, and may be in need of treatment to raise its core temperature. However, it will be appreciated that a mammal need not be hypothermic to be treated by the system of the present invention.

Further, as used herein, the phrase "thermal energy exchange" shall also be understood to mean the transfer of heat from the thermal core of a mammal to the system of the invention. More specifically, a "thermal energy exchange" includes the transfer of heat from the thermal core of the mammal to a treated body portion and then to the system of the invention. In other words, "thermal energy exchange" may also encompass cooling of the core temperature of a mammal by the system of the invention. In this context, the mammal may be hyperthermic and in need of treatment to lower its core body temperature.

Figure 1:
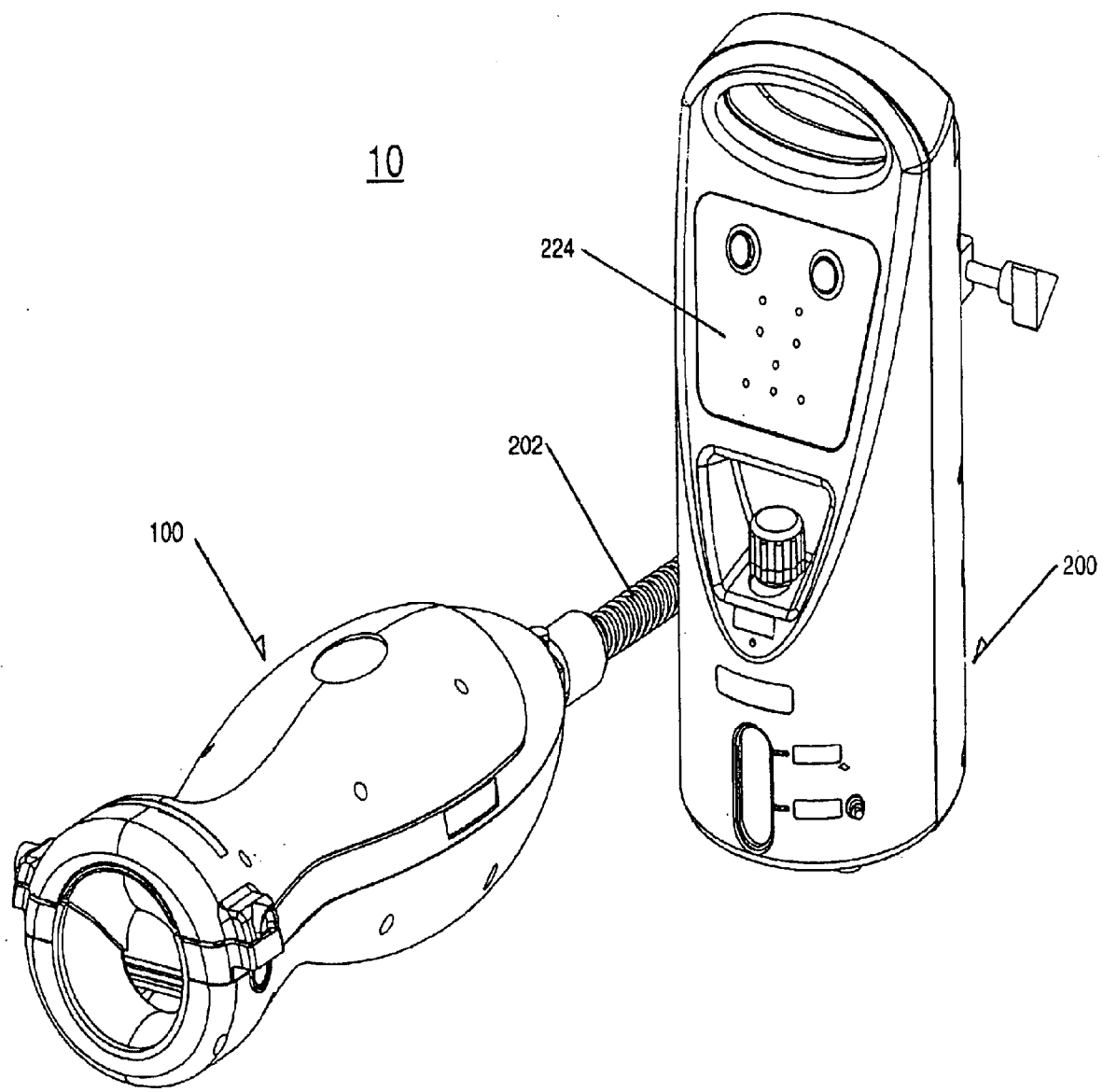
FIG. 1 is an exemplary system for manipulating the core body temperature of a mammal.

In accordance with an exemplary embodiment of the invention, FIG. 1 illustrates an exemplary system 10 for manipulating the core body temperature of a mammal. The system 10 comprises a thermal energy exchange chamber 100, a control unit 200, and a tubing set 202 for connecting chamber 100 to control unit 200.

Figure 2A:
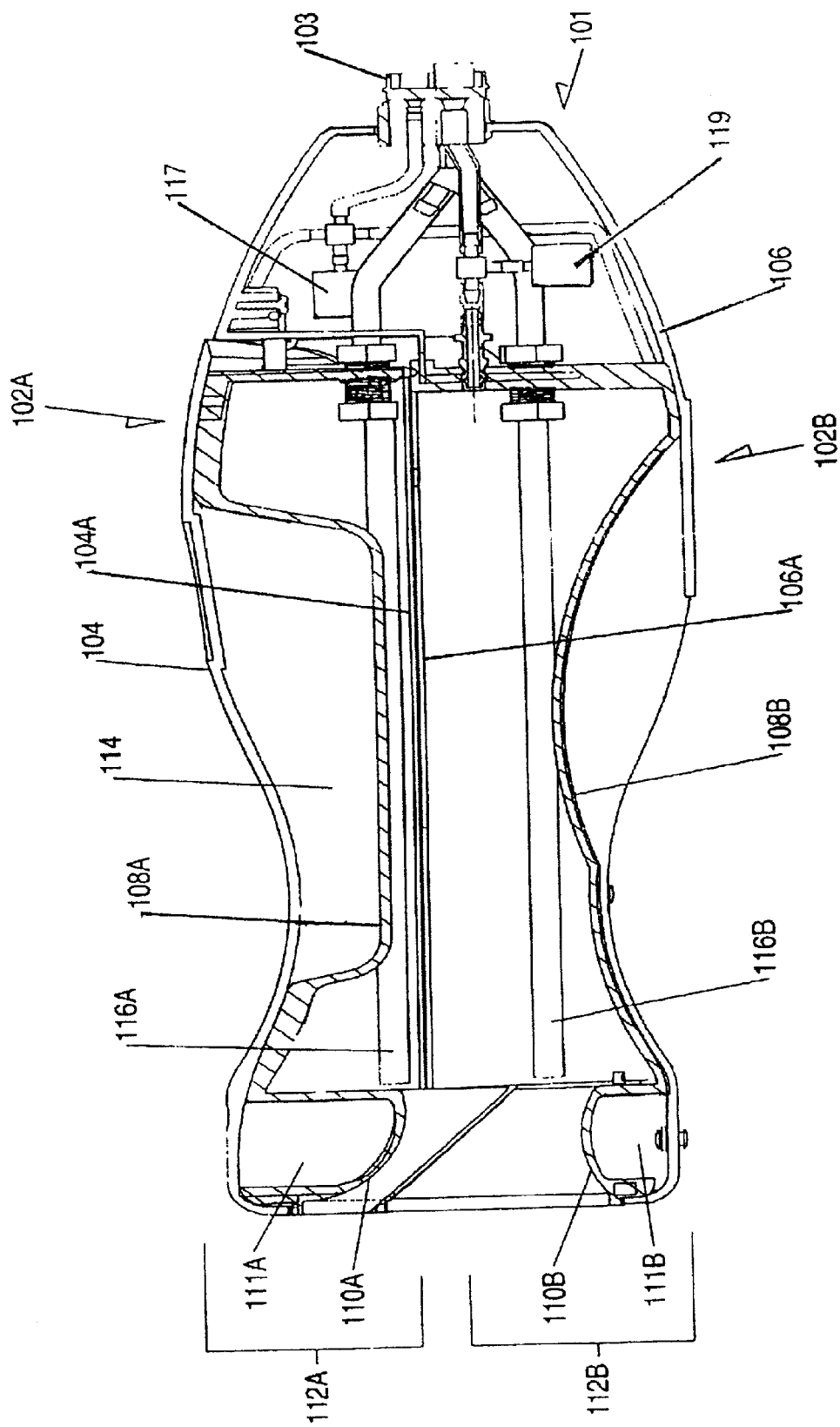
FIG. 2A is a cross-sectional view of an exemplary thermal energy exchange chamber in accordance with the invention.
Figure 2B:
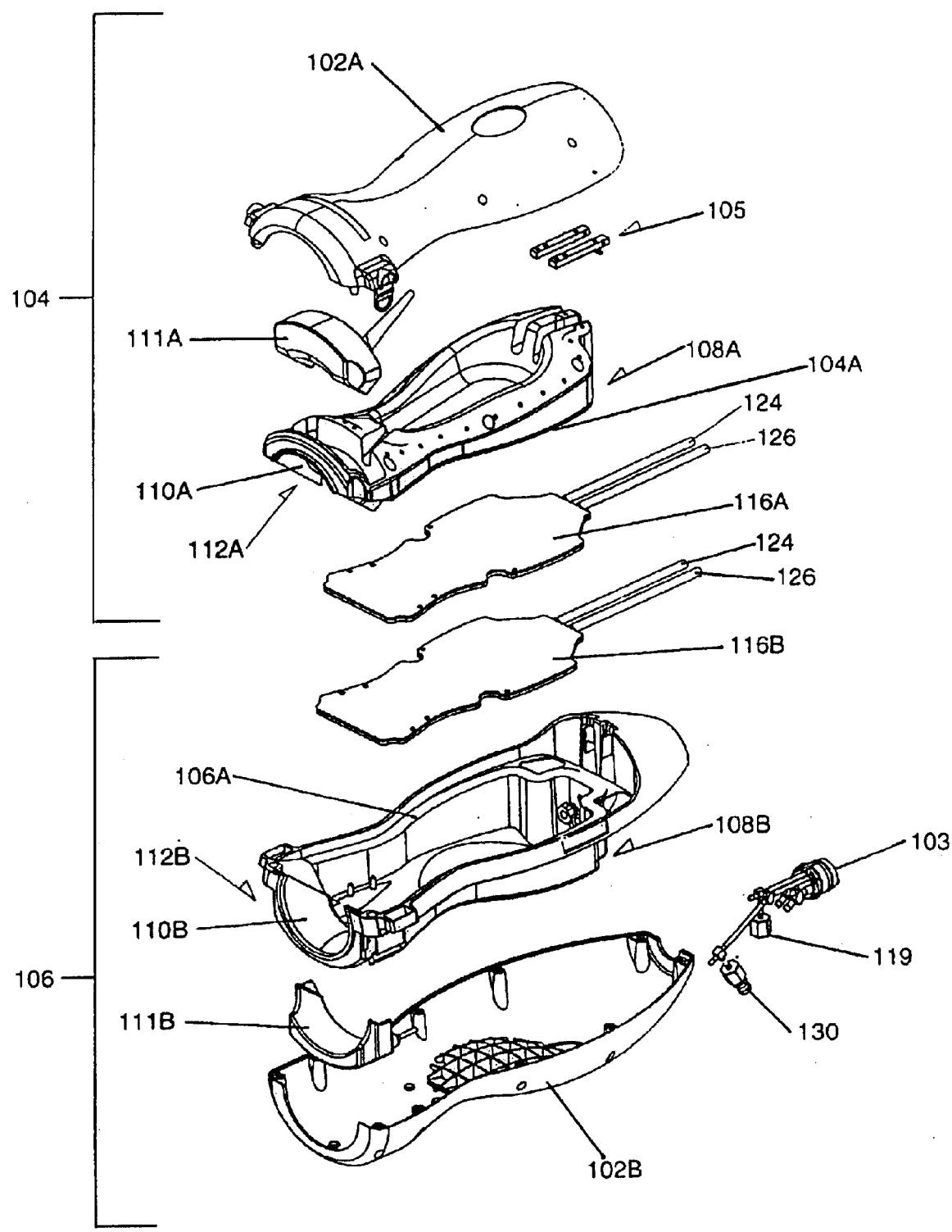
FIG. 2B is an exploded view of the exemplary embodiment of FIG. 2A.

FIGS. 2A and 2B illustrate a cross-sectional view and an exploded view, respectively, of an exemplary thermal energy exchange chamber 100. Chamber 100 may be adapted for the treatment of human patients, as well as other mammals. Chamber 100 may be adapted to conform to any suitable body portion. In one embodiment, a suitable body portion may comprise an extremity, including a portion of an extremity, such as an arm, a portion of an arm, a leg, a portion of a leg, and/or the like. In another embodiment, a suitable body portion may include a head, a neck, or a torso. In an exemplary embodiment, chamber 100 is configured to exchange thermal energy with a body portion comprising specialized subcutaneous heat-exchange vasculature, such as the relatively hairless regions of the hands and feet, for example. In one embodiment, chamber 100 is shaped and sized to fit almost any adult. In an alternate embodiment, chamber 100 is shaped and sized to fit a child. In still another embodiment, chamber 100 is sized and shaped to fit a mammal other than a human. In an exemplary embodiment, chamber 100 is configured to conform to an arm or a portion of an arm (such as a hand and a forearm, for example) and is further configured to be ambidextrous.

In an exemplary embodiment, chamber 100 comprises an elongated, substantially concave moveable member 104 adapted to engage an elongated, substantially concave base member 106. Moveable member 104 may be coupled to base member 106 in any suitable fashion. In one embodiment, moveable member 104 is pivotally coupled (such as by a hinge 105, for example, or other suitable coupling device which facilitates the pivotal engagement of two components) to the base member 106 at a distal end 101 of the chamber 100, thereby permitting the moveable member 104 to reciprocably and matingly engage the base member 106. In another embodiment, moveable member 104 may be pivotally coupled (such as by a hinge or other suitable device) to the base member 106 at a side of the chamber 100. In yet another embodiment, moveable member 104 may be freely disengageable from base member 106 such that moveable member 104 and base member 106 are separate, uncoupled components that may be brought into proximity with each other and be matingly engaged with one another to form chamber 100. In either of these embodiments, moveable member 104 may be moved toward base member 106 to encase the body portion within the chamber 100 and then be moved away from base member 106 to permit removal of the body portion from the chamber 100. In this manner, the chamber 100 permits placement of a body portion onto base member 106, enclosure of the body portion within the chamber 100, and removal of the body portion from the base member 106 and the chamber 100.

Moveable member 104 includes a first outer shell member 102A and base member 106 includes a second outer shell member 102B. First outer shell member 102A and second outer shell member 102B are configured to engage each other upon engagement of moveable member 104 and base member 106 so that the operable components of chamber 100 are enclosed by a protective, durable housing. First and second outer shell members 102A and 102B are configured to engage a connector 103 for attachment to tubing set 202. As further described below, connector 103 is associated with valves and/or other connections to a plurality of conduits including conduits for: supplying positive pressure to the chamber 100, supplying a vacuum to evacuate the chamber 100, and supplying and circulating fluid from the control unit 200 and through the chamber 100. First and second outer shell members 102A and 102B may be made of any durable material, including elastomers, polypropylene, composite materials, graphite, fiberglass, lightweight metal alloys (such as aluminum or titanium alloys, for example), and the like. In one embodiment, first and second outer shell members 102A and 102B are made of a rigid thermoplastic material.

Chamber 100 may comprise any suitable fastener for securing moveable member 104 to base member 106. Exemplary fasteners may include straps, cords, hooks, clips, clamps, latches, pins, magnetic gaskets, and/or any other suitable mechanism configured to maintain secure engagement of members 104 and 106 while chamber 100 is in use. In one embodiment, the engagement of members 104 and 106 is maintained by a strap that surrounds chamber 100 and is tightened to keep members 104 and 106 together. In a further embodiment, chamber 100 comprises a mechanism for alternately locking and releasing first outer shell member 102A and second outer shell member 102B, thereby permitting the opening and closing of chamber 100. This mechanism may comprise mechanical latches, spring-loaded fasteners, quick disconnect fasteners, and the like, as described above. In one embodiment, the mechanism comprises a single device which facilitates locking and releasing the members 104 and 106.

In accordance with the invention, chamber 100 further comprises a first flexible membrane 108a and a second flexible membrane 108b. In an exemplary embodiment, first flexible membrane 108a is over-molded to an interior surface of first outer shell member 102A, and second flexible membrane 108b is over-molded to an interior surface of second outer shell member 102B. In this embodiment, when moveable member 104 and base member 106 are brought together to form a chamber, a sealing surface 104a at the peripheral edge of flexible membrane 108a contacts a sealing surface 106a at the peripheral edge of flexible membrane 108b to permit sealing of the moveable member 104 to the base member 106 during use of the chamber 100. In an alternative embodiment, first flexible membrane 108a and second flexible membrane 108b may be connected integrally to form a single, continuous membrane that completely envelopes the body portion placed within the chamber 100.

Flexible membranes 108a and 108b are configured to enhance the surface contact between energy elements 116a and 116b, described below, and the body portion placed within the chamber 100. That is, when the vacuum system 204b, described below with reference to FIG. 6, operates via the vacuum port 117 (illustrated in FIG. 5) to produce a sub-atmospheric pressure within the chamber 100, first flexible membrane 108a and second flexible membrane 108b collapse against energy elements 116a and 116b, respectively, and facilitate thermal energy exchange between the energy elements 116a and 116b and the body portion placed within the chamber 100. Flexible membranes 108a and 108b may comprise any flexible material that is biocompatible (and therefore safe for contact with the skin of a mammal) and capable of producing a consistently airtight seal. Suitable materials may include, for example, gas permeable thermoplastic and/or elastomeric materials, such as C-FLEX® (Consolidated Polymer Technologies, Inc., Largo, Fla.), DynaFlex (GLS Corporation, McHenry, Ill.), and other elastomeric materials with similar properties. In a preferred aspect, flexible membranes 108a and 108b comprise material that is temperature resistant.

Figure 6:
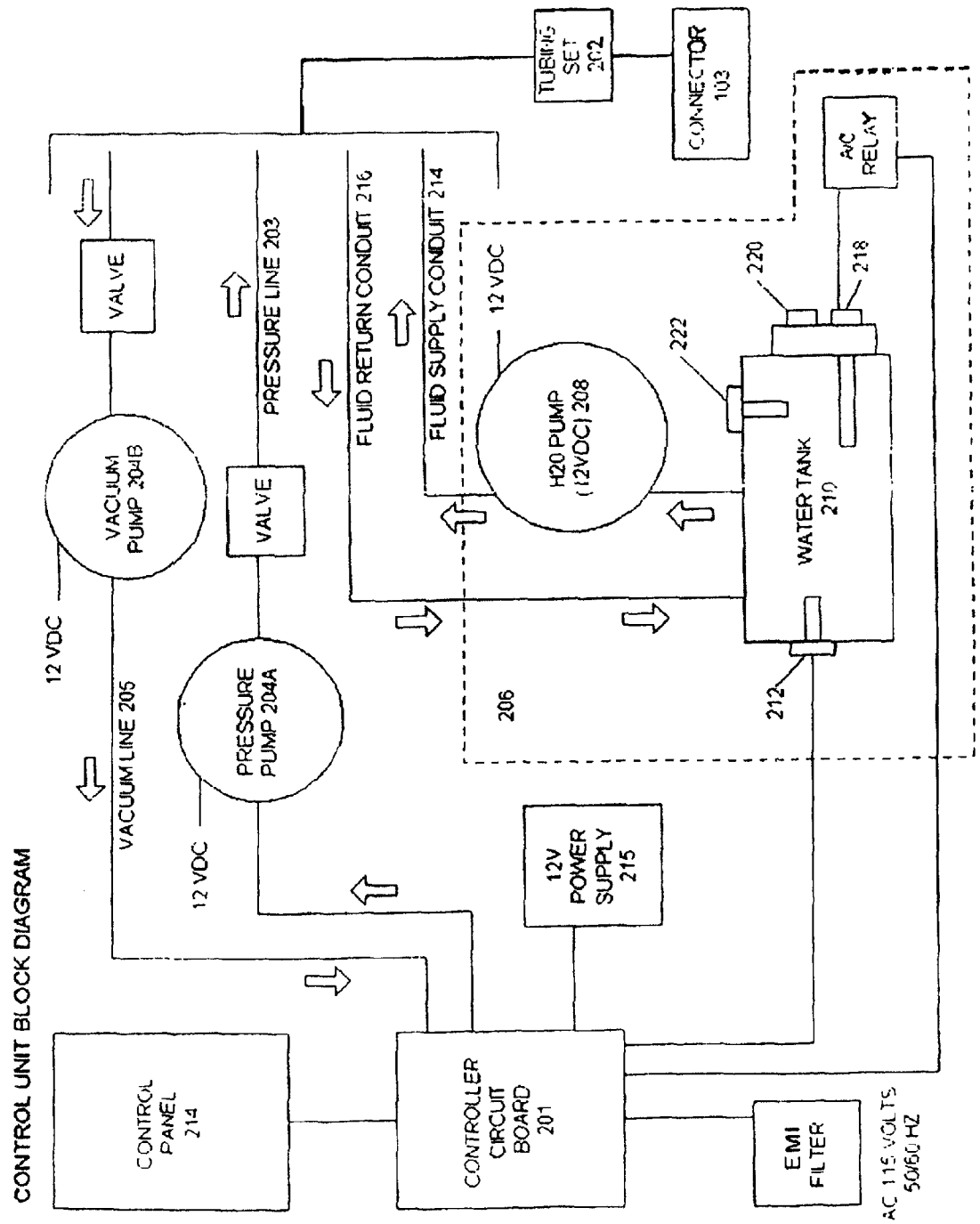
FIG. 6 is a schematic block diagram illustrating an exemplary control unit in accordance with the invention.

In accordance with another embodiment of the invention, chamber 100 further includes a first cuff 110a and a second cuff 110b. First cuff 110a is integrally formed of first flexible membrane 108a and is positioned at a proximate end 112a of the interior surface of moveable member 104. Second cuff 110b is integrally formed of second flexible membrane 108b and is positioned at a proximate end 112b of the interior surface of base member 106. First cuff 110a and second cuff 110b are configured to enclose a body portion within chamber 100 when moveable member 104 and base member 106 are closed together, such that the sub-atmospheric pressure created by the vacuum system 204b of FIG. 6 may be maintained within the chamber 100. First cuff 110a and second cuff 110b are further configured to accommodate the varying sizes and shapes of body portions placed within chamber 100 and to provide a seal around the body portion which does not significantly constrict blood flow to and from the body portion. In one embodiment, first cuff 110a and second cuff 110b exert sufficient pressure around and against the body portion such that the body portion is inhibited from moving relative to the chamber 100 while the pressure system 204a of FIG. 6 is in operation.

Figure 5:
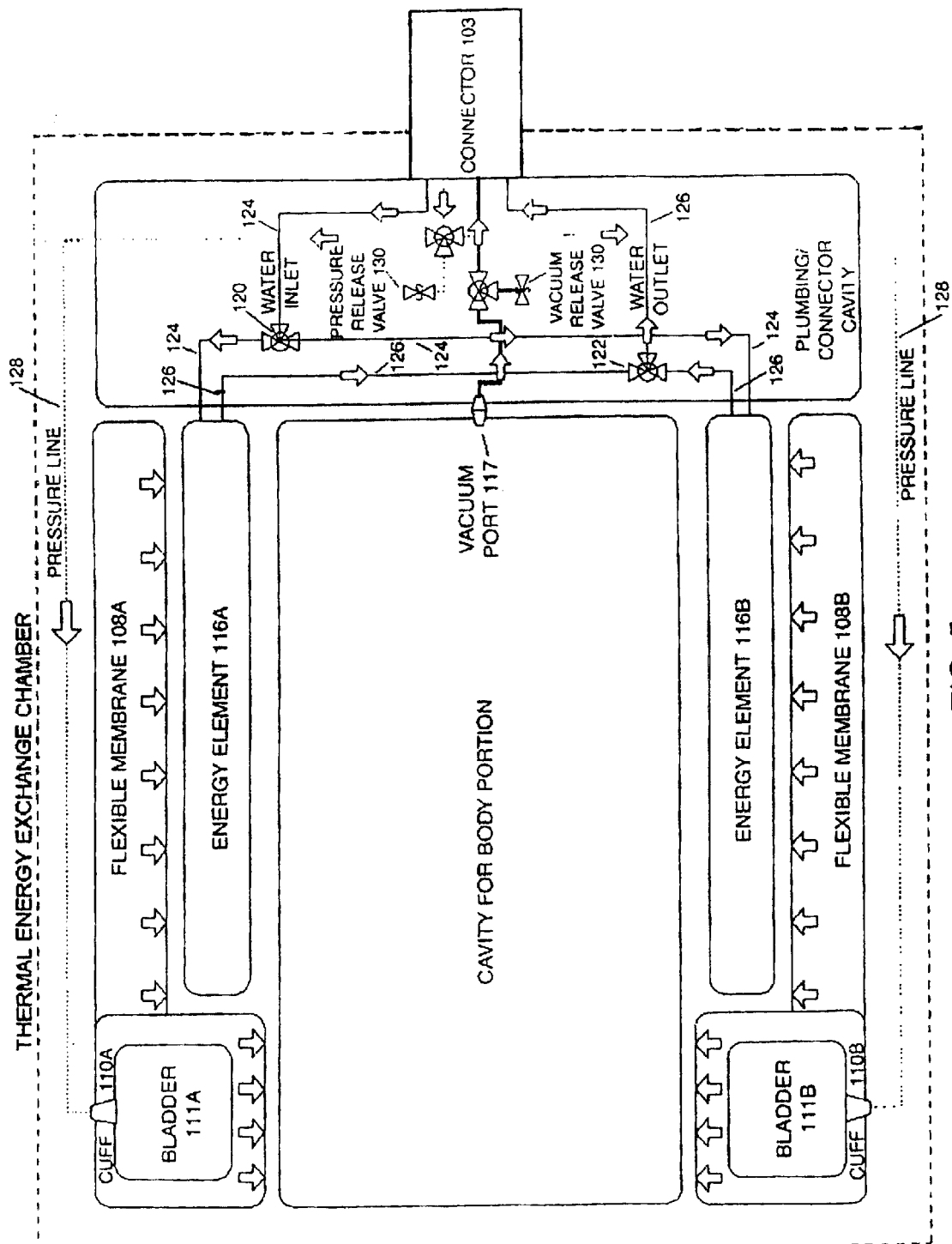
FIG. 5 is a schematic block diagram illustrating an exemplary thermal energy exchange chamber in accordance with the invention.

In an exemplary embodiment, first cuff 110a at least partially encases a first bladder 111a, and second cuff 110b at least partially encases a second bladder 111b. In one embodiment, when system 10 is to be used, positive pressure is applied to first bladder 111a and second bladder 111b from control unit 200 to expand or inflate first cuff 110a and second cuff 110b and to form a pneumatic seal around a body portion placed within the chamber 100. The positive pressure may be provided by any suitable fluid, including a gas such as air, for example. As illustrated in FIG. 5, first and second bladders 111a and 111b are each connected to connector 103 by a pressure line 128. Pressure line 128 may be any suitable type of conduit, including tubing, which may be either flexible or rigid. As further illustrated in FIG. 6, connector 103 receives positive pressure from pressure system 204a via conduit 203 and tubing set 202.

When a body portion is to be removed from chamber 100, first and second bladders 111a and 111b are deflated to release the body portion from the chamber 100. In one embodiment, the deflation of bladders 111a and 111b is initiated by the deactivation of the pressure system 204a of FIG. 6. The inherent elasticity of the bladder material releases the pressure on the body portion as the fluid pressure is released from within the bladders to establish equilibrium with ambient air pressure. In one embodiment, the contraction mechanism is effected by pressure system 204a of FIG. 6 through activation of a pressure release valve 130 (illustrated in FIG. 5) within the chamber 100.

In an exemplary embodiment, the operation of bladders 111a and 111b is automatically controlled by control unit

200. In another embodiment, bladders 111*a* and 111*b* may be expanded in accordance with one of a plurality of predetermined size settings, such as small, normal, and large for example, to accommodate patients of varying sizes. Selection of an appropriate setting on the control unit 200 establishes a predetermined pressure associated with the bladders 111*a* and 111*b* and the enclosure created between first cuff 110*a* and second cuff 110*b* when chamber 100 is closed, such that the enclosure is adaptable to the circumference and contour of the body portion placed within the chamber 100. In this manner, the enclosure created by first cuff 110*a* and second cuff 110*b* creates a seal around the body portion placed within the chamber 100 and prevents undesirable movement of the body portion within the chamber 100 during operation of the system.

In another exemplary aspect, bladders 111*a* and 111*b* provide for a rate of decay of the sub-atmospheric pressure within the chamber 100 of less than about 10 mmHg per minute while the pressure system 204*a* and the vacuum system 204*b* of FIG. 6 are in operation. In a further aspect, bladders 111*a* and 111*b* permit the vacuum system 204*b* to achieve a pre-selected level of sub-atmospheric pressure inside the chamber 100 within about 15–30 seconds after activating the power switch 226 (FIG. 7A) on control unit 200. As described in greater detail below, vacuum system 204*b* produces a pre-selected sub-atmospheric pressure within chamber 100 that is between about −10 mmHg and about −400 mmHg, preferably between about −20 mmHg and about −85 mmHg, and more preferably between about −20 mmHg and about −30 mmHg, relative to atmospheric pressure.

Referring again to FIGS. 2A and 2B, in accordance with the invention, chamber 100 further comprises energy elements 116*a* and 116*b*. Energy elements 116*a* and 116*b* may be any suitable device for the controlled exchange or transfer of thermal energy from one source to another, such as a blanket or a pad that is configured to carry heating or cooling fluid for example. Other sources of thermal energy may also include sources of electromagnetic radiation (such as microwave radiation or infrared radiation), radiant or electric heaters, ultrasonic pulses, conduction due to an exothermic reaction, and/or the like. In an exemplary embodiment, each of energy elements 116*a* and 116*b* is contiguous with an interior portion of flexible membranes 108*a* and 108*b*, respectively, and contacts the body portion placed within the chamber 100. During operation of the system 10, the sub-atmospheric pressure created by vacuum system 204*b* of FIG. 6 causes the flexible membranes 108A and 108B to collapse against the energy elements 116A and 116B establishing and maintaining contact between the energy elements 116A and 116B and the surface of the body portion. The vacuum system 204*b* of FIG. 6 continues to draw air away from the body portion while maintaining a pressure differential relative to the ambient air. As illustrated in FIG. 5, energy elements 116*a* and 116*b* are each connected to a fluid inlet 120 and a fluid outlet 122 by fluid supply conduits 124 and fluid return conduits 126, respectively. The fluid supply conduits 124 and fluid return conduits 126 connect the energy elements 116*a* and 116*b* to the fluid inlet 120 and fluid outlet 122, respectively, as well as to connector 103. In an exemplary embodiment, fluid supply conduits 124 and fluid return conduits 126 comprise flexible, temperature-resistant tubing. In a preferred aspect, energy elements 116*a* and 116*b* comprise material that is biocompatible and therefore safe for contact with the skin of a mammal.

In an exemplary embodiment, energy elements 116*a* and 116*b* are perfusion pads that effect the exchange of thermal energy between the system 10 and the body portion placed within the chamber 100 by being constantly perfused with a temperature-regulated fluid that is circulated by control unit 200, as described in greater detail below with reference to FIG. 6. In another embodiment, energy elements 116*a* and 116*b* may include perforations through non-fluid containing portions of the energy element which allow the even removal of air pressure by the vacuum system over a wider surface area and thereby minimize the trapping of air between the energy element and the body portion.

In one exemplary embodiment, energy elements 116*a* and 116*b* are heating elements which effect the transfer of heat from the system of the invention to the body portion placed within the chamber 100. It will be appreciated, however, that energy elements 116*a* and 116*b* may comprise any suitable heating structure, such as heating coils encased in a thermal exchange blanket for example. As the vacuum system 204*b* of FIG. 6 produces a sub-atmospheric pressure within chamber 100 and induces dilation of the vascular structures (i.e., arteriovenous anastomoses (AVA's), capillaries, and thermal exchange vasculature) within the body portion, energy elements 116*a* and 116*b* transfer heat to the surface of the body portion. Since vasodilated capillaries readily absorb heat, the sub-atmospheric pressure coupled with the heating element results in the efficient absorption of thermal energy through the skin of the body portion and, consequently, the transport of that energy via the vascular system and the blood stream to the thermal core of the mammal.

In one embodiment, energy elements 116*a* and 116*b* comprise perfusion pads which are continuously perfused with a heated fluid (not shown). The heated fluid may be any inert, non-volatile and/or non-flammable fluid, including liquids such as water, for example. In an exemplary embodiment, the surface temperature of energy elements 116*a* and 116*b* is maintained at a temperature of from about 35° C. to about 48° C. and is preferably from about 42.5° C. to about 43.5° C. Energy elements 116*a* and 116*b* that comprise perfusion pads may be made of any suitable heat-resistant material, such as polyester, urethane, nylon, and the like. In one embodiment, energy elements 116*a* and 116*b* may comprise flexible perfusion pads that are made of urethane material and contain interstitial spaces through which the fluid may flow while acting as a heat exchanger.

In another exemplary embodiment, energy elements 116*a* and 116*b* may comprise cooling elements. In this embodiment, energy elements 116*a* and 116*b* enable a transfer of heat from the body portion placed within the chamber 100 to the cooling energy elements 116*a* and 116*b*. In an exemplary embodiment, energy elements 116*a* and 116*b* may comprise perfusion pads which are continuously perfused with a cooling fluid that serves to lower the core body temperature of the mammal when the pressure system 204*a* is activated. The cooling fluid may be any inert, nonvolatile and/or non-flammable fluid, including liquids such as water, for example. In an exemplary embodiment, the surface temperature of energy elements 116*a* and 116*b* is maintained at a temperature of from about 5° C. to about 37° C. and preferably from about 5° C. to about 12° C. Energy elements 116*a* and 116*b* that comprise perfusion pads may be made of any suitable material, such as polyester, urethane, nylon, and the like. In a further embodiment, energy elements 116*a* and 116*b* may be maintained at a normal body temperature to maintain the core body temperature within a normal body temperature range.

Figure 3:
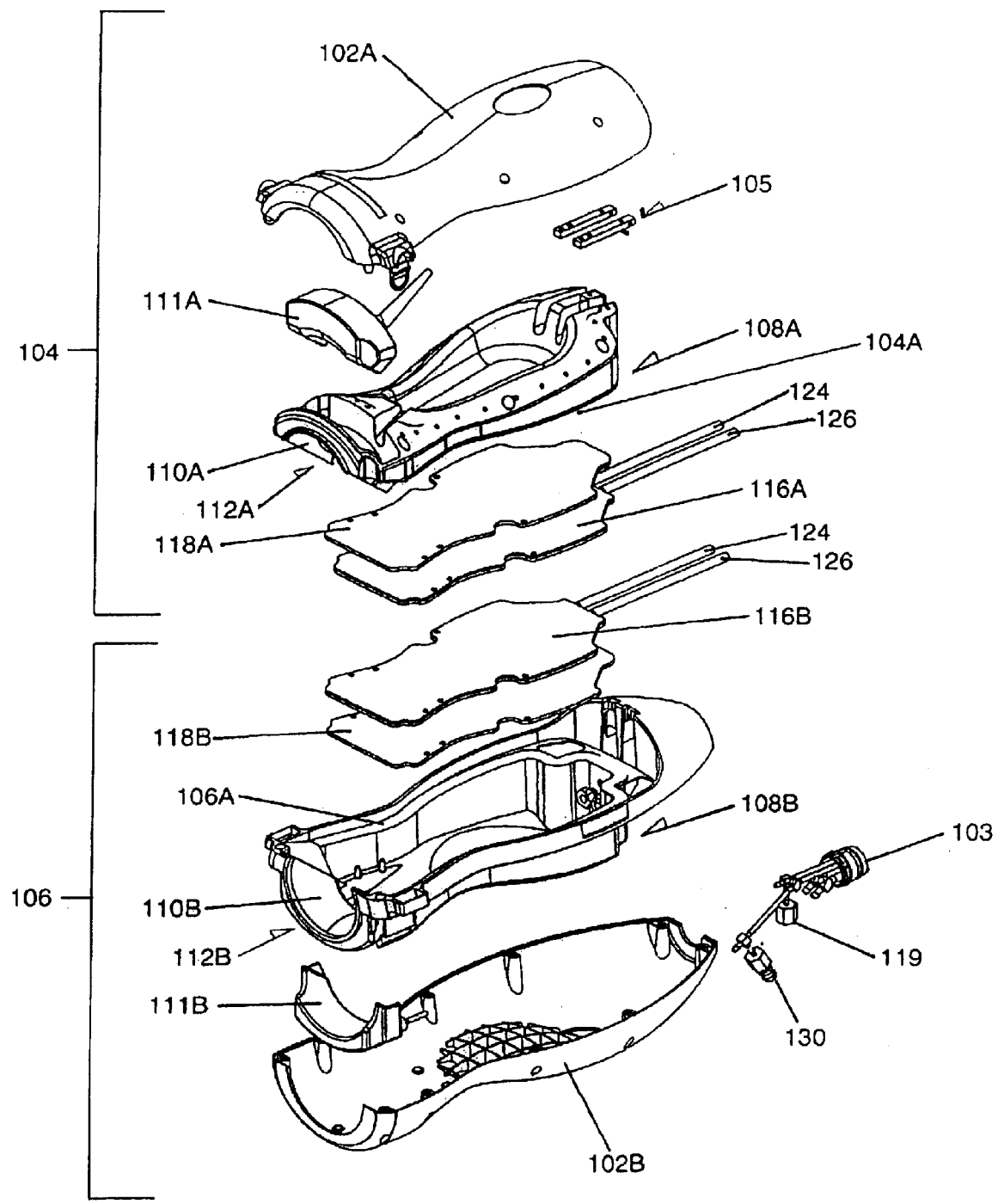
FIG. 3 is an exploded view of another exemplary thermal energy exchange chamber in accordance with the invention.

In another exemplary embodiment, energy elements 116*a* and 116*b* each comprise a backing layer 118*a* and 118*b*, respectively, as illustrated in FIG. 3. Backing layers 118*a* and 118b are contiguous with the energy elements 116a and 116b, respectively, and are each in contact with flexible membranes 108a and 108b, respectively. In an exemplary aspect, backing layers 118a and 118b comprise an insulating material, such as a phase change material for example, which is capable of absorbing heat from energy elements 116a and 116b. In this manner, the temperature within the chamber 100 may be maintained when the heat source, such as control unit 200, has been disconnected from the chamber 100. Suitable phase change material may be obtained from Sea Systems Group, Inc. (Raleigh, N.C.), for example. In an exemplary embodiment, after the system has achieved the pre-selected optimal treatment temperature and has been in operation for at least about 10 minutes, backing layers 118a and 118b permit a temperature degradation of less than about 1% per minute, and preferably less than about 0.5% per minute, within the chamber 100 once the chamber 100 has been disconnected from the heat source and/or control unit 200. The capacity to maintain heat within the chamber 100 permits transport of a patient from, for example, an operating room to a recovery area without requiring termination of the beneficial effects of treatment during the period of transport.

Figure 4:
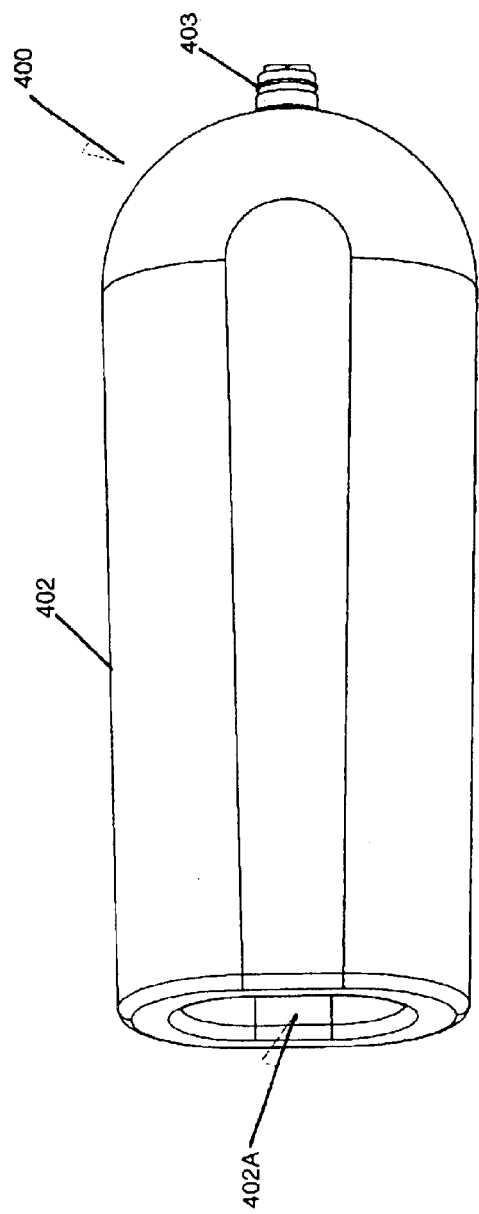
FIG. 4 is a top view of another exemplary thermal energy exchange chamber in accordance with the invention.
Figure 4A:
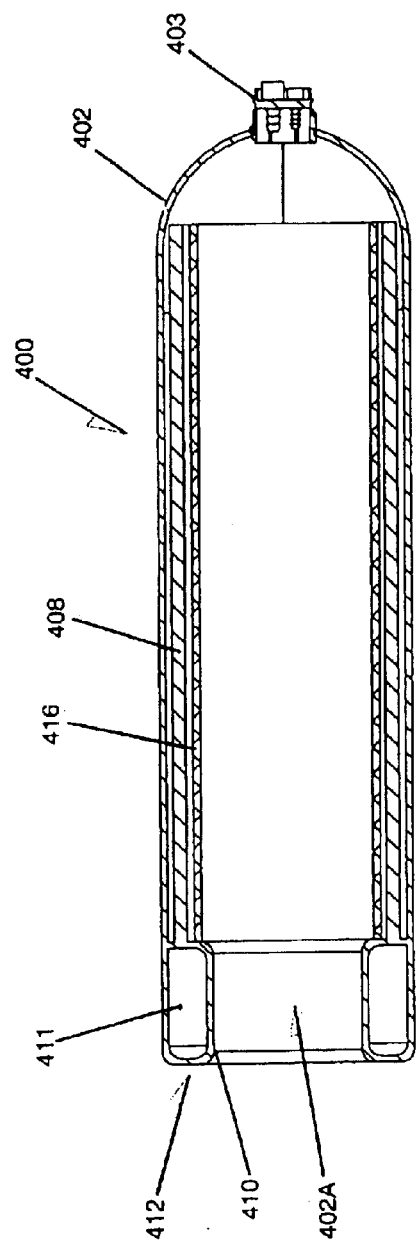
FIG. 4A is a cross-sectional view of the exemplary embodiment depicted in FIG. 4.

FIGS. 4 and 4A illustrate a top view and a cross-sectional view, respectively, of another exemplary thermal energy exchange chamber 400 which may be utilized by the system 10. Chamber 400 is substantially similar to chamber 100, except that chamber 400 comprises an outer shell 402 which is formed of a single, hollow, tubular member having an entry port 402a which facilitates the placement of a body portion within the chamber 400. Outer shell 402 includes a connector 403 for attachment to tubing set 202. Outer shell 402 may be made of any of the materials described above with reference to outer shell 102 of FIGS. 2A and 2B. In this embodiment, the lack of an additional seal interface, such as the interface between sealing surfaces 104a and 106a of FIGS. 2A and 2B, eliminates a potential path through which undesirable fluid and/or gaseous interchanges between the chamber 400 and the external environment may take place.

As illustrated in FIG. 4A, chamber 400 further comprises a flexible membrane 408. In an exemplary embodiment, flexible membrane 408 is over-molded to an interior surface of outer shell 402 and forms a single, continuous membrane that completely envelopes a body portion (not shown) placed within the chamber 400. Flexible membrane 408 is configured to enhance the surface contact between an energy element 416, described below, and the body portion placed within the chamber 400. That is, when the vacuum system 204b, described below with reference to FIG. 6, operates to produce a sub-atmospheric pressure within the chamber 400, flexible membrane 408 facilitates thermal energy exchange between the energy element 416 and the body portion placed within the chamber 400 by collapsing against the energy element 416 and enabling the energy element 416 to conform to the body portion. Flexible membrane 408 may comprise any of the materials described above with reference to flexible membranes 108a and 108b of FIGS. 2A and 2B.

In an exemplary embodiment, chamber 400 further comprises an annular cuff 410 configured to effect an adjustable, iris-like entry port 402a which is adapted to expand around the body portion preceding a treatment and then relax subsequent to the treatment to allow egress from the chamber 400. Entry port 402a is of suitable diameter to permit insertion of a body portion into the chamber 400. Annular cuff 410 is integrally formed of flexible membrane 408 and is positioned at a proximate end 412 of the interior surface of outer shell 402. Annular cuff 410 is configured to enclose a body portion which is inserted into entry port 402a and placed within chamber 400. Annular cuff 410 is further configured to seal entry port 402a around the body portion such that the sub-atmospheric pressure created by the vacuum system 204b of FIG. 6 may be maintained within the chamber 400. Annular cuff 410 is adapted to accommodate the varying sizes and shapes of body portions placed within chamber 400 and to provide a seal around the body portion which does not significantly constrict blood flow to and from the body portion. In one embodiment, annular cuff 410 exerts sufficient pressure around and against the body portion to inhibit movement of the body portion relative to the chamber 400 while the vacuum system 204b is in operation.

In an exemplary embodiment, annular cuff 410 at least partially encases at least one bladder 411. In one embodiment, when system 10 is to be used, positive fluid pressure is applied to bladder 411 from control unit 200 to expand or inflate annular cuff 410, forming a pneumatic seal around a body portion placed within the chamber 400. Bladder 411 is connected to connector 403 and control unit 200 in a manner similar to that described above with reference to chamber 100.

In an exemplary embodiment, the operation of bladder 411 is automatically controlled by control unit 200. In another embodiment, bladder 411 may be expanded in accordance with one of a plurality of predetermined settings, such as small, normal, and large for example, to accommodate patients of varying sizes. Selection of an appropriate setting on the control unit 200 establishes a predetermined pressure associated with the entry port 402a, such that the entry port 402a is adaptable to the circumference and contour of the body portion. In this manner, the annular cuff 410 comprises a seal around the body portion placed within the chamber 400 and prevents undesirable movement of the body portion in relation to chamber 400 during operation of the system. In an exemplary embodiment, bladder 411 provides for a rate of decay of the sub-atmospheric pressure within the chamber that is similar to that described above with reference to bladders 111a and 111b of FIGS. 2A and 2B. Bladder 411 also may permit the vacuum system 204b of FIG. 6 to achieve a pre-selected level of sub-atmospheric pressure inside the chamber 400 within about 15–30 seconds after activating the power switch 226 (FIG. 7A) on control unit 200. When a body portion is to be removed from chamber 400, bladder 411 is deflated to release the body portion from the chamber 400. Deflation of bladder 411 may be accomplished in a manner similar to that described above with reference to bladders 111a and 111b of FIGS. 2A and 2B.

In accordance with the invention, chamber 400 further comprises an energy element 416. Energy element 416 may be any suitable device for exchanging or transferring energy from one source to another, such as a blanket or a pad that is configured to carry heating or cooling fluid for example. In an exemplary embodiment, energy element 416 is contiguous with an interior portion of flexible membrane 408 and contacts the body portion placed within the chamber 400. In one embodiment, energy element 416 effects the exchange of thermal energy between the system 10 and the body portion placed within the chamber 400 by being constantly perfused with a temperature-regulated fluid that is circulated by control unit 200, as described in greater detail below with reference to FIG. 5A. Energy element 416 is connected to a fluid inlet, a fluid outlet, fluid supply conduits, and fluid return conduits in a manner similar to that described above with reference to energy elements 116a and 116b of FIGS. 2A and 2B. Energy element 416 may comprise any of the materials described above with reference to energy elements 116a and 116b of FIGS. 2A and 2B.

In another exemplary embodiment, energy element 416 may comprise a backing layer 418. In one embodiment, backing layer 418 comprises an insulating material, such as a phase change material, for example. Backing layer 418 is contiguous with the energy element 416 and is in contact with flexible membrane 408. Backing layer 418 may comprise any of the materials described above with reference to backing layers 118a and 118b of FIG. 3A and therefore provides chamber 400 with similarly advantageous properties.

As will be appreciated, chamber 100 and chamber 400 are but two of several possible embodiments of the present invention. For example, the chamber may be adapted for use around the neck, head, or torso of a patient. In the case of the neck and torso, the chamber may be differentially sized and shaped to accommodate a design that includes two cuffed openings, one on either end of the chamber, and a connector positioned along one of the sides of the chamber, rather than at a distal end of the chamber. This embodiment may include a moveable member that is pivotally coupled to a base member along one side of the chamber, thereby permitting the moveable member to reciprocably and matingly engage the base member in a manner that is similar to that described above with reference to chamber 100. Alternatively, this embodiment may include a moveable member which is freely disengageable from a base member, such that the moveable member and base member are separate, uncoupled components that may be brought into proximity with each other and be matingly engaged with one another to form a chamber. In either of these cases, the chamber may be placed around a neck or a torso, like a collar, and may function in a manner similar to that described above with reference to chamber 100 and chamber 400. It will also be appreciated that a similarly designed chamber may be used to encase a middle portion of an extremity, such as an arm or a leg for example, without encasing the end portion of that extremity, such as the hand or the foot for example.

FIG. 6 is a block diagram of an exemplary control unit 200. The interior of control unit 200 comprises a pressure system 204a, vacuum system 204b, and a thermal energy exchange system 206. In an exemplary embodiment, the control unit 200 comprises a micrologic-controlled, closed-loop feedback system which monitors and regulates the operation of pressure system 204a, vacuum system 204b, and thermal energy exchange system 206. It will be appreciated that control unit 200 may comprise a pressure system 204a and vacuum system 204b that are either separate devices or an integrated device that comprises both systems.

In an exemplary embodiment, the pressure system 204a comprises a conventional, commercially available mechanical air pump which generates positive air pressure. The vacuum system 204b comprises a conventional, commercially available mechanical air pump which generates sub-atmospheric air pressure of at least as low as −400 mmHg. In an exemplary aspect, pressure system 204a delivers, via conduit 203 and tubing set 202, positive pressure to bladders 111a and 111b of FIGS. 2A and 2B to expand first cuff 110a and second cuff 110b around a body portion placed within chamber 100. In another exemplary aspect, vacuum system 204b delivers, via conduit 205 and tubing set 202, sub-atmospheric pressure to chamber 100 to effect mechanical distension of the subcutaneous vascular structures of the body portion placed within the chamber. In one embodiment, vacuum system 204b produces a pre-selected sub-atmospheric pressure within chamber 100 that is between about −10 mmHg and about −400 mmHg, preferably between about −20 mmHg and about −85 mmHg, and more preferably between about −20 mmHg and about −30 mmHg, relative to atmospheric pressure.

In an exemplary embodiment, vacuum system 204b cyclically alternates between generating sub-atmospheric pressure and relieving the vacuum through the vacuum release valve 119 (illustrated in FIG. 5) within the chamber. In this manner, the body portion is exposed alternately to sub-atmospheric pressure and atmospheric pressure during treatment in the chamber 100. In one embodiment, the vacuum system 204b comprises a timing circuit on controller circuit board 201 which permits the vacuum system 204b to alternate between generating sub-atmospheric pressure and permitting the return of atmospheric pressure. The timing circuit may permit vacuum system 204b to establish any pre-selected periods or cycles in which sub-atmospheric pressure and atmospheric pressure are alternated within the chamber 100. Exemplary periods or cycles for the alternating sub-atmospheric and atmospheric pressure may be independently selected from about 30 seconds to about 60 minutes. In an exemplary embodiment, the timing circuit establishes alternating (symmetrical and/or asymmetrical) cycles of sub-atmospheric pressure lasting for about 2 minutes with cycles of atmospheric pressure lasting for about 2 minutes. An alternative embodiment may include varying cycling times, such that the length of the period of sub-atmospheric pressure is different from the length of the period of atmospheric pressure.

In an exemplary embodiment, thermal energy exchange system 206 effects a continual, closed-loop circulation of temperature-regulated fluid through the control unit 200, tubing set 202, and energy elements 116a and 116b of FIGS. 2A and 2B. In one embodiment, thermal energy exchange system 206 comprises a circulation pump 208 connected to a fluid reservoir 210. The temperature of the fluid in reservoir 210 is managed by temperature regulator 212 which is controlled by controller circuit board 201. Fluid reservoir 210 contains any suitable fluid for continual circulation via supply conduit 214 and return conduit 216 through energy elements 116a and 116b of FIGS. 2A and 2B. In one embodiment, while the system is in operation, the fluid circulated by circulation pump 208 flows at a rate of from about 250 milliliters (ml) to about 1 liter (L) per minute and preferably flows at a rate of between about 400 ml to about 600 ml per minute.

In an exemplary embodiment, fluid reservoir 210 stores a heating fluid, such as heated water for example, which is circulated by circulation pump 208 and used to heat energy elements 116a and 116b. In this embodiment, temperature regulator 212 (as controls a fluid-heating element 218 which heats the fluid stored in fluid reservoir 210 to a pre-selected temperature. In one embodiment, while the system is in operation, the fluid in reservoir 210 is maintained at a temperature of from about 35° C. to about 48° C. and preferably is maintained at a temperature of from about 42.5° C. to about 43.5° C. In an exemplary aspect, the fluid in reservoir 210 is brought to a pre-selected treatment temperature by heating element 218, as controlled by temperature regulator 212, within about 1–5 minutes and preferably within about 2–4 minutes after activation of the power switch 226 of FIG. 7A. Heating element 218 may be any suitable heating element, such as a thick-film heater or a cartridge heater, for example. Preferably, heating element 218 is in communication with a bi-metal temperature switch 220 which automatically deactivates the heating element 218 if the temperature regulator 212 malfunctions and the heating element 218 reaches a pre-determined elevated temperature. In one embodiment, the bi-metal switch 220 deactivates heating element 218 when the bi-metal switch 220 registers a temperature of about 48° C.

In an alternate embodiment, fluid reservoir 210 stores a cooling fluid, such as cold water for example, which is circulated by circulation pump 208 and used to cool energy elements 116a and 116b of FIGS. 2A and 2B. In this embodiment, temperature regulator 212 controls a fluid-cooling element 222 which cools the fluid stored in fluid reservoir 210 to a pre-selected temperature. In one embodiment, while the system is in operation, the fluid in reservoir 210 is maintained at a temperature of from about 5° C. to about 37° C. and preferably from about 5° C. to about 12° C. In an exemplary aspect, the fluid in reservoir 210 is brought to a pre-selected treatment temperature by temperature regulator 212 and cooling element 222 within about 1–5 minutes and preferably within about 2–4 minutes after activation of the power switch 226 of FIG. 7A. Cooling element 222 may be any energy exchange system, such as Peltier Effect thermoelectric modules, for example (Kryotherm Company, St. Petersburg, Russia). Preferably, cooling element 222 is in communication with a bi-metal temperature switch 220 which automatically deactivates the cooling element 222 if the cooling element 222 reaches a pre-determined temperature. In one embodiment, the bi-metal switch 220 deactivates cooling element 222 when the cooling element 222 reaches a temperature of about 5° C.

Figure 7B:
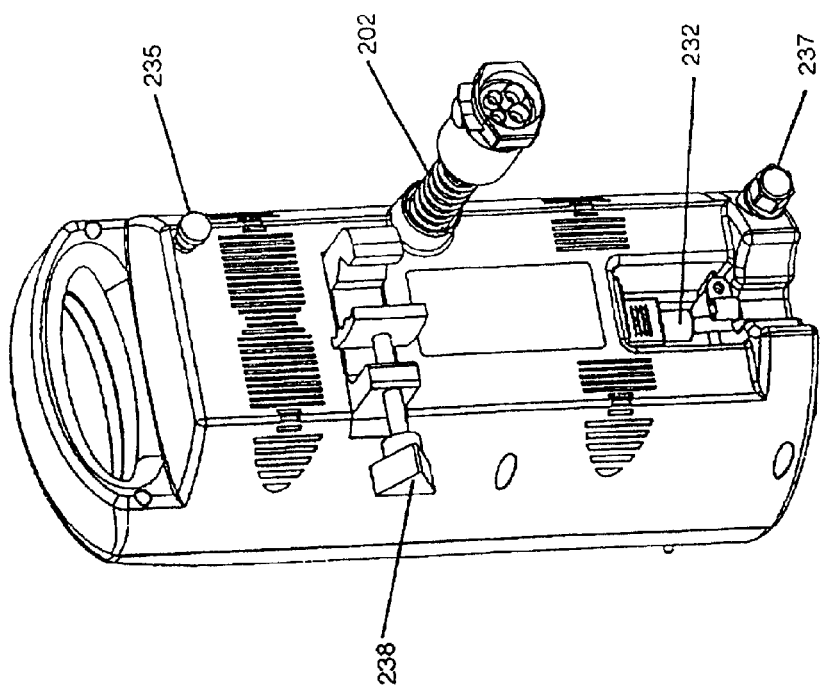
FIGS. 7A and 7B illustrate an exemplary control unit in accordance with the invention.
Figure 7A:
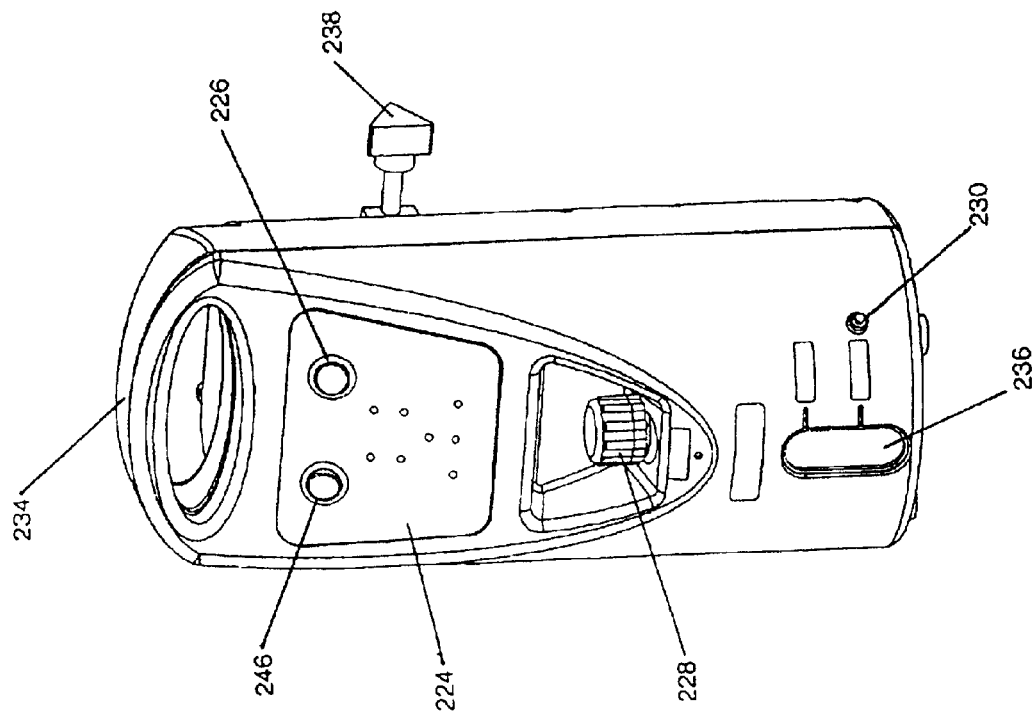
Figure 7C:
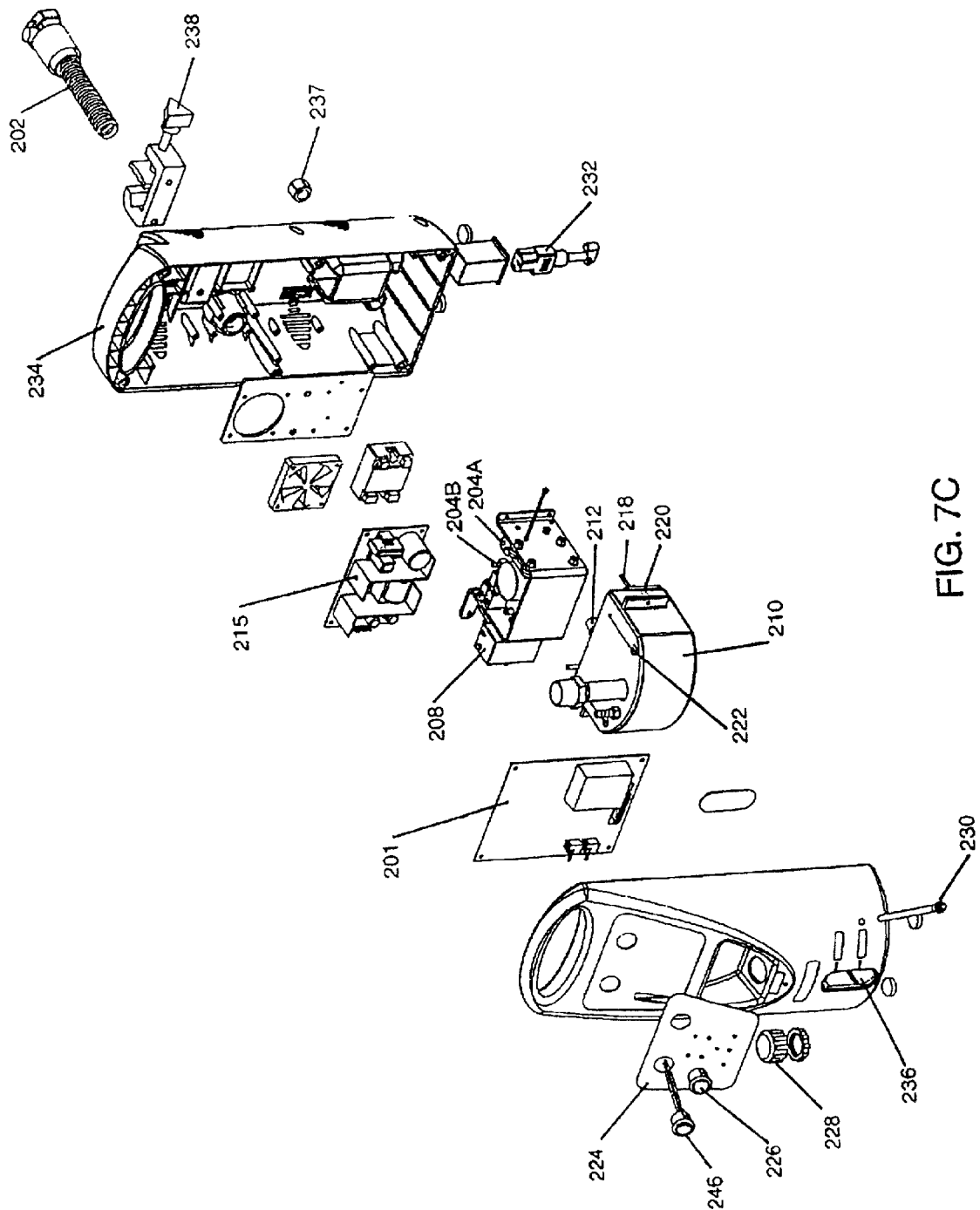
FIG. 7C is an exploded view of the exemplary embodiment of FIGS. 7A and 7B.
Figure 9:
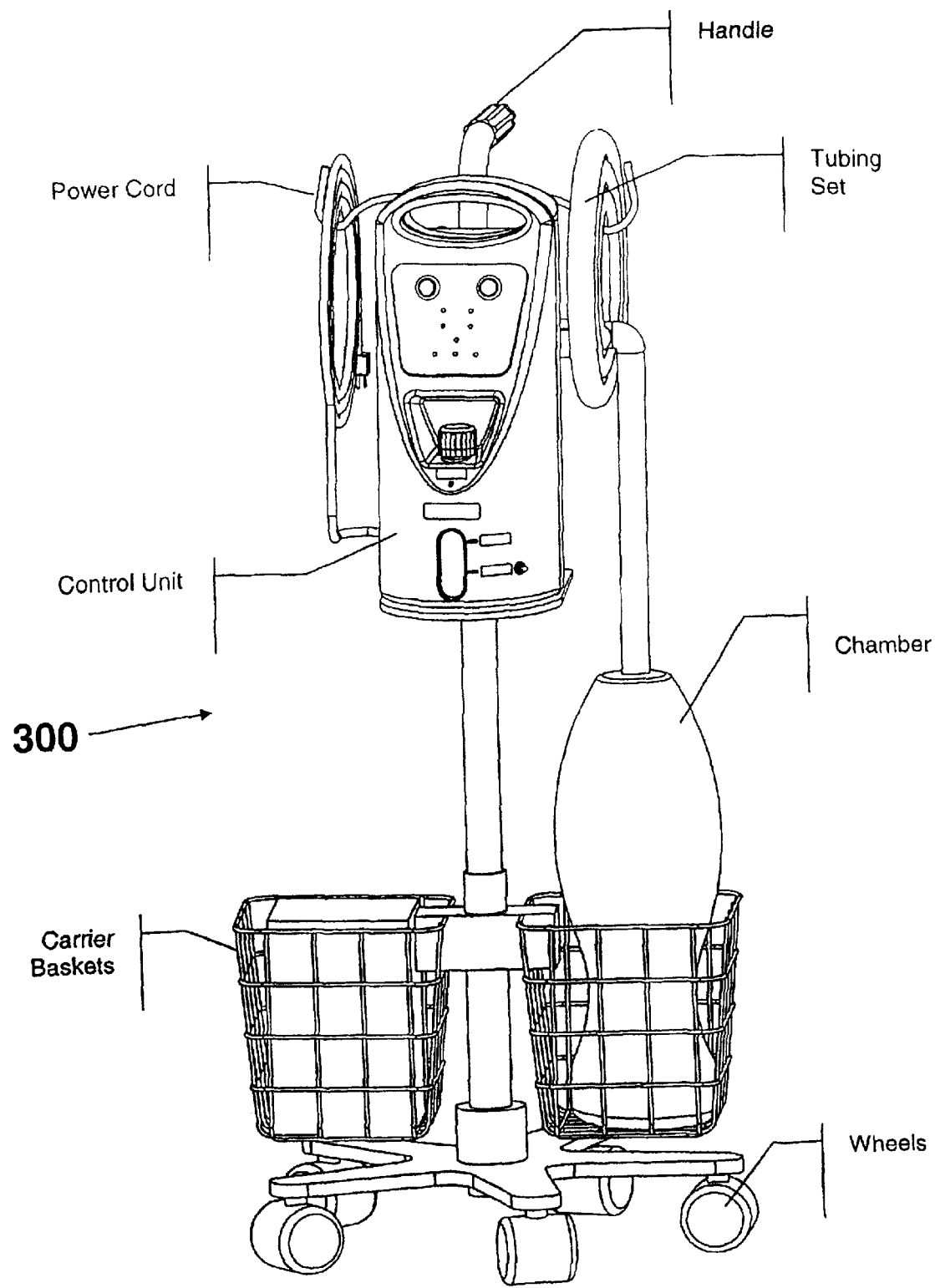
FIG. 9 is an exemplary storage cart for the system of the invention.

FIGS. 7A, 7B, and 7C illustrate front, back, and exploded views, respectively, of an exemplary embodiment of control unit 200. The exterior of control unit 200 comprises a control panel 224; a power switch 226; a fluid inlet port 228 for filling the fluid reservoir 210; a fluid level indicator 230 for indicating whether the fluid reservoir 210 contains sufficient fluid for operation of the system; and a power source connector 232 for connecting control unit 200 to a power source, such as line current or one or more batteries, for example. In alternate embodiments, control unit 200 may also comprise a handle 234, a grounding stud 235, a fluid-level viewing window 236, a drain port 237 for draining fluid reservoir 210, and a mounting system 238 for attaching the control unit 200 to a mounting surface, such as an intravenous (IV) pole, a bed rail, a cart, such as cart 300 illustrated in FIG. 9, and/or the like.

Figure 8:
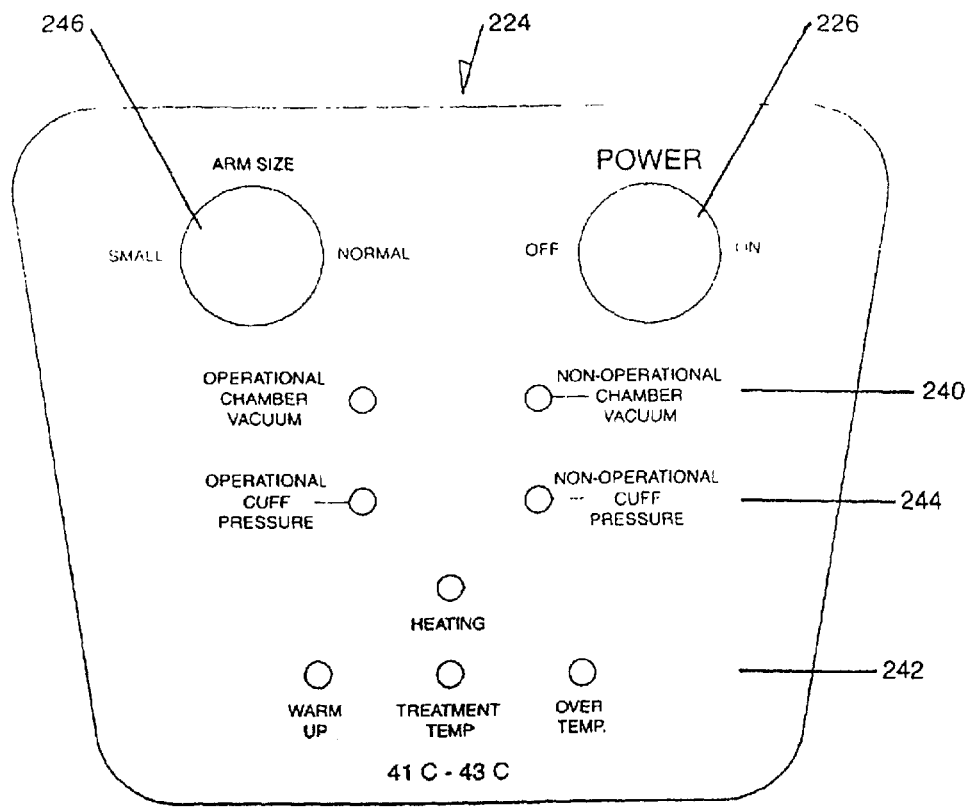
FIG. 8 is an exemplary control panel in accordance with the invention.

In an exemplary embodiment, control panel 224 comprises a plurality of indicators for monitoring the proper functioning of the system 10, such as warning indicators for the pressure system 204a, the vacuum system 204b, and the thermal energy exchange system 206. For example, as illustrated in FIG. 8, control panel 224 may include indicators of vacuum status 240, temperature status 242, and seal status 244 (such as for cuffs 110a and 110b of FIGS. 2A and 2B, for example). Control panel 224 may also comprise a size selector 246 for selecting an appropriate pressure associated with bladders 111a and 111b, as described above with reference to FIGS. 2A and 2B.

In an exemplary aspect, the system provides that electrical components are maintained within control unit 200 and are therefore isolated from patient contact. In addition, the system may include any of a plurality of other features for protecting a patient undergoing treatment by the system. For example, the system may be programmed such that if a predetermined maximum operating temperature is exceeded, the thermal energy exchange system 206 is deactivated and any sub-atmospheric pressure produced within chamber 100 is released via vacuum release valve 119 of FIG. 5. Moreover, an audible alarm and/or a visual indicator on control panel 224 may be activated to warn the system operator that the system has malfunctioned. In an exemplary embodiment, when the fluid temperature exceeds a preset temperature, such as about 46.5° C. for example, the thermal energy exchange system 206 is automatically deactivated and may not be reactivated until the fluid temperature is once again within an acceptable range. In an alternate embodiment, when the fluid temperature is lower than a preset temperature, such as about 5° C. for example, the thermal energy exchange system 206 is automatically deactivated and may not be reactivated until the fluid temperature is once again within the acceptable range.

Additionally, safety functions of the system may be configured such that if a predetermined maximum operating pressure, whether positive or sub-atmospheric, within either the chamber or the bladder(s) is exceeded, the pressure system 204a and vacuum system 204b are deactivated, the vacuum within the chamber is released, and the thermal energy exchange system 206 is deactivated. Moreover, an audible alarm and/or a visual indicator on control panel 224 may be activated to warn the system operator that the system has malfunctioned. For example, when the pressure within the chamber is lower than about −85 mmHg, the mechanical vacuum release valve 119 may be set to automatically release the pressure, and the chamber returns to atmospheric pressure. In an exemplary embodiment, the vacuum release valve 119 may be configured to open at a predetermined sub-atmospheric pressure, such as about −129 mmHg for example.

The mechanical pressure release valve 130 (illustrated in FIG. 5) prevents over-pressurization of the bladder(s) in the event of a circuit failure in the controller circuit board 201, which can cause pressure system 204a to allow too much air pressure into the bladder(s). Moreover, when the pressure within the bladder(s) exceeds a pre-selected pressure associated with a setting of size selector 246 of FIG. 8, seal status indicator 244 and/or an audible alarm may be activated. For example, when the pressure within the bladder(s) exceeds about 65 mmHg for a "small" arm setting on selector 246 or exceeds about 45 mmHg for a "normal" arm setting on selector 246, an alarm is activated, and a system operator may then open the chamber to reposition the arm of the patient.

Figure 10:
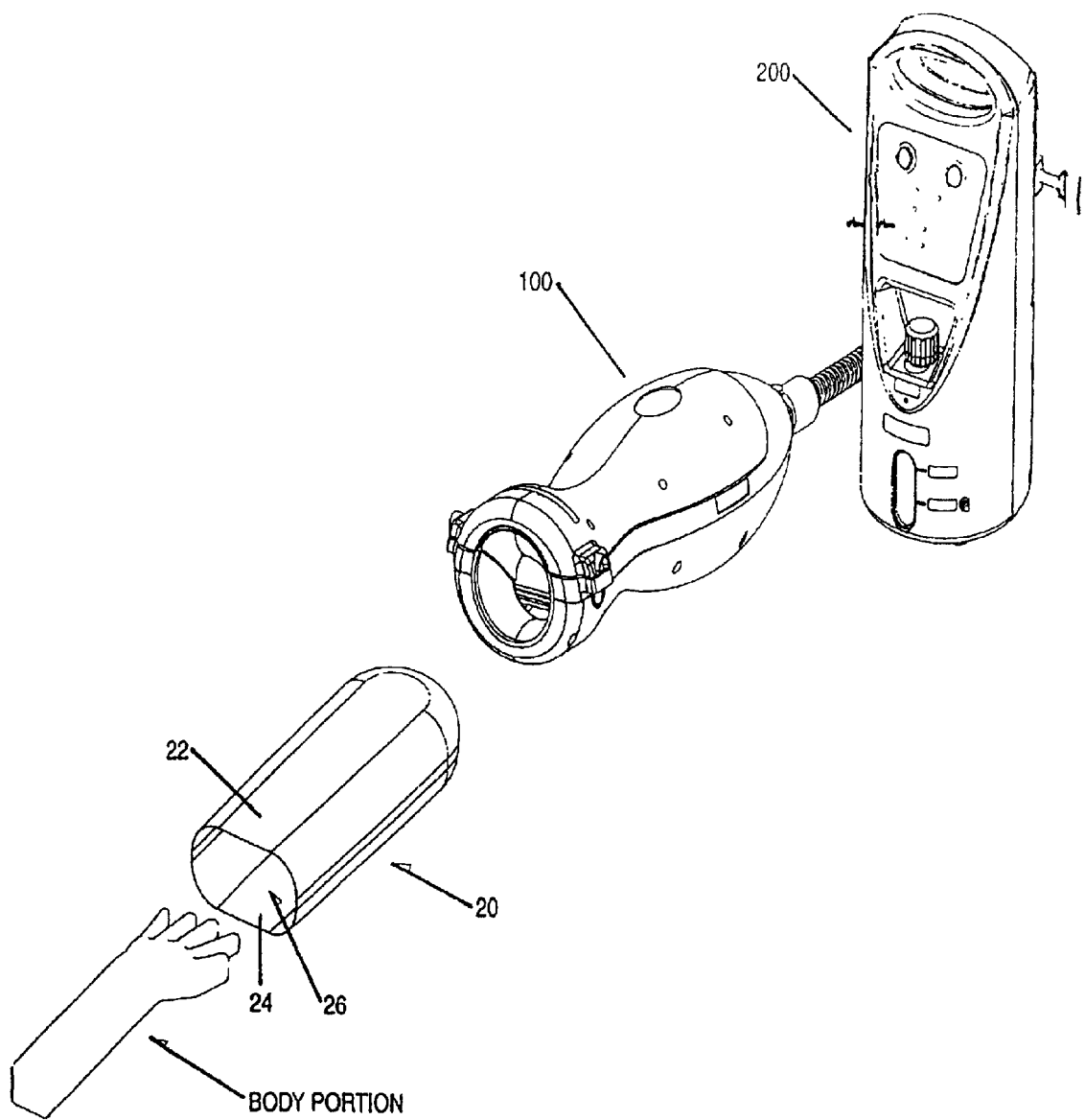
FIG. 10 illustrates an exemplary sleeve which may be used in conjunction with the system of the invention.

In accordance with another exemplary embodiment of the present invention, system 10 may further comprise a sleeve 20 as illustrated in FIG. 10. Sleeve 20 may be used to cover a body portion prior to placing the body portion within the chamber 100. In an exemplary aspect, sleeve 20 provides a barrier to moisture transmission and inhibits contamination of the interior compartment of chamber 100. For example, use of a sleeve 20 limits contamination of the interior of chamber 100 by any bodily fluids (such as from perspiration) and/or particulate matter that may be associated with the body portion placed within the chamber 100. In one embodiment, sleeve 20 is disposable and therefore is discarded after a single use.

In an exemplary aspect, sleeve 20 permits air flow between the interior of sleeve 20 and the interior of chamber 100. That is, sleeve 20 permits air that may be trapped between the body portion and the sleeve 20 to flow through the sleeve 20 when the vacuum system 204b operates to create a sub-atmospheric pressure within the chamber 100. In one embodiment, sleeve 20 comprises a gas permeable material. In another embodiment, sleeve 20 comprises a vent which permits the flow of air out of the sleeve 20. In a further embodiment, sleeve 20 comprises an elastic material which facilitates application of sleeve 20 over the body portion of the patient. Sleeve 20 comprises material which is biocompatible and preferably hypoallergenic.

In an exemplary embodiment, sleeve 20 comprises a top layer 22 and a bottom layer 24 which are connected to each other to form a pocket 26 in which a body portion may be placed prior to being placed into the chamber 100. Layers 22 and 24 may comprise any temperature resistant, biocompatible material, such as urethane. The layers 22 and 24 may be connected in any suitable manner, such as by stitching, gluing, or heat-bonding for example. In another embodiment, top layer 22 is transparent so that the surface of the body portion may readily be viewed when the chamber 100 is opened without requiring the removal of the body portion from the sleeve 20. In another embodiment, at least one of layers 22 and 24 is impregnated with a silver compound which enhances the transfer of thermal energy (i.e., heat) between the energy elements 116a and 116b of FIGS. 2A and 2B and the body portion enveloped in the sleeve 20. In still another embodiment, phase change material is associated with at least one of layers 22 and 24 such that sleeve 20 may retain some quantity of heat once removed from the chamber 100. In a preferred aspect, bottom layer 24 is bonded to the phase change material.

In accordance with an aspect of the invention, the system may be used to manipulate the core body temperature of a mammal, such as a human for example. In an exemplary embodiment, the system may be used either to raise or lower the core body temperature of a mammal. If the core body temperature of the patient is to be raised, the patient may be either normothermic or hypothermic prior to treatment by the system. If the core body temperature of the patient is to be lowered, the patient may be either normothermic or hyperthermic prior to treatment by the system. It should be understood that the exemplary method described herein for using the system of the invention merely presents one such method and is not intended to limit the scope of the invention as described above.

In an exemplary embodiment, referring to FIGS. 1, 2A, 2B, 5, 6, 7A, 7C, and 10, operation of the system 10 begins by suitably filling the fluid reservoir 210 via fluid inlet port 228 and suitably connecting tubing set 202 to both the chamber, such as chamber 100 for example, and the control unit 200. Fluid may be added to the reservoir 210 to ensure that an appropriate level of fluid is maintained in the reservoir 210. In an exemplary embodiment, to begin treatment of a patient, the chamber 100 is opened by raising moveable member 104, and the body portion of the patient is then suitably positioned within the chamber 100. In a preferred aspect, the body portion is positioned such that optimal contact between the body portion and the energy elements 116a and 116b is achieved. In one embodiment, the body portion may be inserted into a sleeve 20 prior to placement of the body portion within the chamber 100. The moveable member 104 is then lowered such that optimal contact is made with base member 106, and the chamber 100 is suitably sealed via the pressure system 204a. The power switch 226 is then depressed to activate both the pressure system 204a and the vacuum system 204b, and treatment of the patient begins.

Power switch 226 activates the main systems of control unit 200, such as pressure system 204a, vacuum system 204b, and thermal energy exchange system 206. Initially, pressure system 204a is activated to expand bladders 111a and 111b such that a pressure associated with the selected size setting is produced around the body portion without constricting blood flow to the body portion. Once an appropriate pressure has been established around the body portion, thereby providing an air-tight seal around the body portion, vacuum system 204b is activated to cyclically maintain a sub-atmospheric pressure within the chamber 100 that ranges from about −10 mmHg to about −400 mmHg, preferably from about −20 mmHg to about −85 mmHg, and more preferably from about −20 mmHg to about −30 mmHg, relative to atmospheric pressure. Vacuum system 204b alternates the pressure within the chamber 100 between sub-atmospheric pressure and atmospheric pressure through a timing circuit. In one embodiment, a cycle of sub-atmospheric pressure ranging from about −20 mmHg to about −30 mmHg lasts for about 2 minutes, followed by a cycle of atmospheric pressure for about 2 minutes, and then another cycle of sub-atmospheric pressure, etc., for the duration of the treatment. A treatment may last for any suitable length of time. In an exemplary embodiment, a treatment may last from about 15 minutes to about 4 hours.

Simultaneously with the activation and operation of pressure system 204a, thermal energy exchange system 206 is activated. Temperature regulator 212 ensures that the fluid in reservoir 210 is within the pre-selected temperature range, and pump 208 continuously circulates the fluid through fluid supply conduit 214, tubing set 202, fluid supply conduit 124 to the energy elements 116a and 116b, and then back through the fluid return conduits 126 and 216 to reservoir 210. In an exemplary embodiment, temperature regulator 212 ensures that the fluid circulating through the system is in the range of from about 35° C. to about 48° C. and preferably in the range of from about 42.5° C. to about 43.5° C. In an alternate embodiment, temperature regulator 212 ensures that the fluid circulating through the system is in the range of from about 5° C. to about 37° C. and preferably in the range of about 5° C. to about 12° C. It will be appreciated that, while the thermal energy exchange system 206 is described as activating simultaneously with the activation of pressure system 204A, thermal energy exchange system 206 may also be activated after activation of pressure system 204A, that is, after an appropriate pressure has been established in bladders 111A and 111B.

At the conclusion of a patient's treatment, power switch 226 is set at the "off" position, which causes deactivation of pressure system 204a, vacuum system 204b, and thermal energy exchange system 206. In particular, the air pressure pump is deactivated, any accumulated sub-atmospheric pressure within chamber 100 is released through vacuum release valve 119, and any positive air pressure within bladders 111a and 111b is also released through pressure release valve 130. Additionally, the thermal energy exchange system 206, including fluid circulation pump 208, are also suitably deactivated. Once atmospheric pressure has been reestablished within the chamber 100, moveable member 104 is separated from base member 106, such as by pivoting around a hinge mechanism for example, and the body portion is removed from chamber 100. Sleeve 20, if used, is then subsequently removed from the body portion.

It will be appreciated that although various aspects of the invention, such as aspects of control unit 200 for example, are frequently described herein with specific reference to the components of chamber 100, these references are non-limiting and are merely for purposes of convenience, clarity, and simplicity. These aspects of the invention are equally applicable to chamber 400, as well as other embodiments of the thermal energy exchange chamber of the invention.

The foregoing specification describes the invention with reference to specific embodiments. However, it will be appreciated that various modifications and changes can be made without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical".

We claim:

1. A system for manipulating a core body temperature of a mammal, the system comprising:
    a chamber for enclosing a body portion of a mammal, said chamber comprising:
        a base member having a first distal end and a first sealing surface;
        a moveable member adapted to matingly, engage said base member; wherein the moveable member has a second distal end pivotally mounted to said first distal end of the base member and a second sealing surface which reciprocably contacts said first sealing surface to enclose said body portion within said chamber, and
    a fastener adapted to maintain engagement of said base member with said moveable member, wherein the movable member moves toward the base member to enclose the body portion in the chamber and the moveable member moves away from the base member to remove the body portion from the chamber;
    a seal in operative association with said chamber for sealing said chamber around said body portion and for inhibiting movement of said body portion relative to said chamber when the system is in operation;
    a thermal energy exchange system in operative association with said chamber, wherein said thermal energy exchange system comprises an energy element assembly coupled to a flexible membrane assembly, wherein said flexible membrane assembly (i) facilitates an exchange of energy between said energy element assembly and said body portion and (ii) comprises a first flexible membrane associated with an interior surface of said moveable member and a second flexible membrane associated with an interior surface of said base member, wherein said first flexible membrane and said second flexible membrane are each configured to enhance surface contact between said energy element assembly and said body portion; and wherein said energy element assembly comprises a first energy element in association with said first flexible membrane and a second energy element in association with said second flexible membrane; wherein said first energy element and said second energy element are adapted to enable an exchange of energy via said body portion between each of said first energy element and said second energy element and said thermal core of said mammal; and
    a vacuum system operatively associated with said chamber while said thermal energy exchange system is in operation, wherein said vacuum system generates a sub-atmospheric pressure within said chamber.

2. The system of claim 1, wherein said body portion is one of an extremity, part of an extremity, a head, a neck, and a torso.

3. The system of claim 1, to wherein said seal comprises:
    a first cuff positioned at a proximate end of said interior surface of said moveable member; and
    a second cuff positioned at a proximate end of said interior surface of said base member;
    wherein said first cuff and said second cuff are configured to surround said body portion when said moveable member contacts said base member to enclose said body portion within said chamber.

4. The system of claim 3, wherein said seal further comprises:
    a first bladder at least partially encased within said first cuff; and
    a second bladder at least partially encased within said second cuff;
    wherein said first bladder and said second bladder are configured to form a pneumatic seal around said body portion during operation of the system.

5. The system of claim 4, wherein said first bladder and said second bladder are operatively associated with a pressure system which provides positive pressure to expand said first bladder and said second bladder around said body portion during operation of the system.

6. The system of claim 1, wherein each of said first energy element and said second energy element is further adapted to enhance surface contact with said body portion.

7. The system of claim 1, wherein said first energy element and said second energy element each comprises one of a heating element and a cooling element.

8. The system of claim 1, wherein said first energy element and said second energy element are each configured to maintain a surface temperature of from about 5° C. to about 48° C.

9. The system of claim 1, wherein said thermal energy exchange system further comprises at least one backing layer which is contiguous with at least one of said first energy element and said second energy element and contacts at least one of said first flexible membrane and said second flexible membrane.

10. The system of claim 9, wherein said at least one backing layer comprises an insulating material.

11. The system of claim 10, wherein said insulating material comprises a phase change material.

12. The system of claim 1, wherein said thermal energy exchange system further comprises:
    a circulation pump;
    a fluid reservoir in operative association with said circulation pump; and
    a temperature regulator coupled to said fluid reservoir.

13. The system of claim 12, wherein each of said first energy element and said second energy element each comprises a perfusion pad which is configured to be perfused with a temperature-regulated fluid.

14. The system of claim 13, wherein said temperature-regulated fluid is a liquid.

15. The system of claim 14, wherein said liquid is water.

16. The system of claim 1, wherein said selected sub-atmospheric pressure is from about −10 mmHg to about −400 mmHg, relative to atmospheric pressure.

17. The system of claim 16, wherein said vacuum system alternates between generating said selected sub-atmospheric pressure and permitting a return to atmospheric pressure within said chamber during operation of the system.

18. The system of claim 1, further comprising a sleeve into which said body portion is inserted prior to enclosement within said chamber.

19. The system of claim 18, wherein said sleeve comprises a first layer which is attached to a second layer to form a pocket into which said body portion is placed.

20. The system of claim 19, wherein said first layer is transparent.

21. The system of claim 19, wherein at least one of said first layer and said second layer is impregnated with a silver compound.

22. The system of claim 19, wherein at least one of said first layer and said second layer is associated with an insulating material.

23. The system of claim 22, wherein said insulating material comprises a phase change material.

24. The system of claim 1, wherein
the base member has a first side and a first sealing surface; and
a moveable member has a second side pivotally mounted to said first side and a second sealing surface which reciprocably contacts said first sealing surface to enclose said body portion within said chamber.

25. The system of claim 24, said flexible membrane assembly comprising a first flexible membrane associated with an interior surface of said moveable member and a second flexible membrane associated with an interior surface of said base member, wherein said first flexible membrane and said second flexible membrane are each configured to enhance surface contact between said energy element and said body portion.

26. The system of claim 25, wherein said seal comprises:
a first cuff positioned at a proximate end of said interior surface of said moveable member;
a second cuff positioned at a proximate end of said interior surface of said base member;
a third cuff positioned at a distal end of said interior surface of said moveable member; and
a fourth cuff positioned at a distal end of said interior surface of said base member;
wherein said first and second cuffs are configured to form a first collar and said third and fourth cuffs are configured to form a second collar around said body portion when said moveable member contacts said base member, such that said body portion is enclosed within said chamber.

27. The system of claim 26, wherein said seal further comprises:
a first bladder at least partially encased within said first cuff;
a second bladder at least partially encased within said second cuff;
a third bladder at least partially encased within said third cuff, and
a fourth bladder at least partially encased within said fourth cuff;
wherein said first bladder and said second bladder form a proximate bladder pair, said third bladder and said fourth bladder form a distal bladder pair, and each of said proximate bladder pair and said distal bladder pair is configured to form pneumatic seals around said body portion during operation of the system.

* * * * *